United States Patent [19]

Axelrod

[11] Patent Number: 4,526,917

[45] Date of Patent: Jul. 2, 1985

[54] FLAME RETARDANT MIXTURE OF TRIARYL PHOSPHATES AND RESINOUS COMPOSITIONS THEREOF

[75] Inventor: Robert J. Axelrod, Glenmont, N.Y.

[73] Assignee: General Electric Company, Pittsfield, Mass.

[21] Appl. No.: 582,924

[22] Filed: Feb. 23, 1984

Related U.S. Application Data

[63] Continuation of Ser. No. 161,637, Jun. 20, 1980, abandoned.

[51] Int. Cl.$^3$ .................................................. C08L 71/04
[52] U.S. Cl. .................................... 524/141; 106/177; 260/966; 524/115; 524/136; 524/143; 524/145; 524/508
[58] Field of Search ............... 524/115, 136, 141, 143, 524/145, 508; 106/177; 260/966

[56] References Cited

U.S. PATENT DOCUMENTS

| | | | |
|---|---|---|---|
| 2,126,850 | 8/1938 | Whitehead | 106/177 |
| 3,383,435 | 5/1968 | Cizek | 525/132 |
| 3,639,506 | 2/1972 | Haaf | 524/115 |
| 3,773,864 | 11/1973 | Sullivan | 260/966 |
| 3,859,395 | 1/1975 | Terhune et al. | 260/966 |
| 3,883,613 | 5/1975 | Cooper | 524/115 |
| 3,931,091 | 1/1976 | d'Ostrowick | 260/966 |
| 3,943,087 | 3/1976 | Leuchs | 524/115 |
| 3,943,097 | 3/1976 | Kawagoshi et al. | 524/115 |
| 4,139,487 | 2/1979 | Garrett | 260/966 |

FOREIGN PATENT DOCUMENTS 2027712  2/1980  United Kingdom ............... 260/966

OTHER PUBLICATIONS

Hilado, Flammability Handbook for Plastics, 1969, pp. 82–84.

Derwent, Abstract of German Patent Publication, DT 2929-099, 5/6/80.

*Primary Examiner*—Lester L. Lee
*Attorney, Agent, or Firm*—Hedman, Gibson, Costigan & Hoare

[57] ABSTRACT

Flame retardant admixtures of triaryl phosphates and a resin as well as a process for preparation are described. The triaryl phosphate mixture includes at least one phosphate where 1 or 2 of the 3 aryl groups are mesityl and the remaining group or groups are independently selected from among phenyl and xylyl. The triaryl phosphate mixture provides better flame retardancy per unit weight of phosphorous than, for instance, triphenyl phosphate alone or trimesityl phosphate alone.

23 Claims, No Drawings

FLAME RETARDANT MIXTURE OF TRIARYL PHOSPHATES AND RESINOUS COMPOSITIONS THEREOF

CROSS-REFERENCE TO RELATED APPLICATION

This is a continuation of application Ser. No. 161,637, filed June 20, 1980, now abandoned.

This invention relates to a flame retardant composition including a mixture of triaryl phosphates, to a resinous composition including a resin moiety and the flame retardant composition, and to a process for preparing the resinous composition.

BACKGROUND OF THE INVENTION

Haaf, U.S. Pat. No. 3,639,506, discloses a blend of polyphenylene ether and a styrene resin characterized by the addition of a flame retardant combination comprising an aromatic phosphate and an aromatic halogen compound. The Haaf patent, incorporated herein by reference, discloses a wide variety of phosphates for use as the aromatic phosphate component of the blend, indicates a preference for triaryl phosphates, and states that the most preferred phosphate is triphenyl phosphate. Cooper, U.S. Pat. No. 3,883,613, incorporated herein by reference, discloses that trimesityl phosphate functions very effectively as a flame retardant per se in compositions of a polyphenylene ether and a styrene resin.

It has now been found that effective flame retardancy is provided by a new mixture of triaryl phosphates which includes at least one such phosphate wherein 1 or 2 of its 3 aryl groups are mesityl groups and its remaining group or groups are independently selected from the phenyl group and xylyl groups. It has further been found that, in resinous compositions containing a resin moiety and the mixture, the flame retardancy of the mixture per unit weight of phosphorus is greater than that of either triphenyl phosphate (TPP) per se or trimesityl phosphate (TMP) per se. Advantageously, this increased flame retardancy is obtained where the resin moieties are compositions of polyphenylene ethers and styrene resins. The latter compositions are known in the art and are described in the above-referenced Haaf and Cooper patents and in Cizek, U.S. Pat. No. 3,383,435, which is incorporated herein by reference.

DESCRIPTION OF THE INVENTION

Generally stated, the present invention provides in one aspect thereof a flame retardant composition comprising a mixture of aromatic phosphates with the mixture being represented by the following average formula:

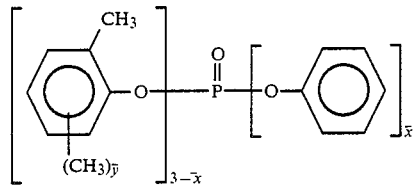

where $\bar{x}$ is a whole or fractional number from slightly more than 0 to slightly less than 3 and $\bar{y}$ is a whole or fractional number from 1 to 2.

In another aspect, generally stated, this invention provides a process for decreasing the self-extinguishing time of a normally flammable resinous composition, said process comprising adding to said resinous composition an effective flame retardant amount of the flame retardant composition set forth above.

Generally stated, in still another aspect, this invention provides a resinous composition comprising (A) a resin moisty and (B) an effective, flame retardant amount of the flame retardant composition set forth above.

Practice of this invention will be better understood by referring to the following detailed description.

DETAILED DESCRIPTION OF THE INVENTION AND MANNER AND PROCESS OF MAKING AND USING IT

Aromatic phosphates which may be included in the mixture of aromatic phosphates include, for example, triphenyl phosphate (TPP), diphenyl mesityl phosphate (DPMP), dimesityl phenyl phosphate (DMPP, trimesityl phosphate (TMP), trixylyl phosphate (TXP), dixylyl mesityl phosphate (DXMP), dimesityl xylyl phosphate (DMXP), and trimesityl phosphate.

In a preferred embodiment, $\bar{y}$ is 2 and the flame retardant mixture comprises at least 2 compounds selected from the group consisting of (a) triphenyl phosphate (TPP), (b) diphenyl mesityl phosphate (DPMP), (c) dimesityl phenyl phosphate (DMPP) and (d) trimesityl phosphate (TMP) subject to the proviso that at least one of said two compounds is selected from the group consisting of DPMP and DMPP. Preferably the mixture comprises at least 3 of said compounds, and more preferably all 4 of said compounds.

In another preferred embodiment $\bar{y}$ is 1 and the flame retardant mixture comprises at least 2 compounds selected from the group consisting of (a) trixylyl phosphate (TXP), (b) dixylyl mesityl phosphate (DXMP), (c) dimesityl xylyl phosphate (DMXP) and (d) trimesityl phosphate (TMP) subject to the proviso that at least one of said 2 compounds is selected from the group consisting of DXMP and DMXP. Preferably the mixture comprises at least 3 of said compounds, and more preferably 4 of said compounds.

The flame retardant composition may further include, in admixture with the mixture having the above average formula, (isopropyl phenyl) phosphates, e.g. tri(isopropyl phenyl)phosphate, such as commercially available Kronitex K-50.

The resin moiety of the resinous composition includes one or more normally flammable resins which are capable of being improved with respect to flame retardancy by the addition thereto of substituted or unsubstituted triarylphosphates. It is well known in the art that such resins include, for example, polyvinyl chlorides, polyphenylene ethers, cellulosic resins, and many polyesters.

In a preferred embodiment, the resin moiety of the resinous composition comprises a normally flammable composition comprising (i) a polyphenylene ether of the formula

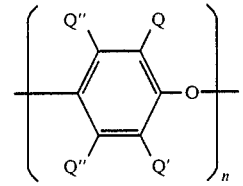

wherein the oxygen ether atom of one unit is connected to the benzene nucleus of the next adjoining unit; Q is a monovalent substituent selected from hydrogen, a hydrocarbon radical, a halohydrocarbon radical having at least two carbon atoms between the halogen atom and the phenol nucleus, hydrocarbonoxy radicals and halohydrocarbonoxy radicals having at least two carbon atoms between the halogen atom and the phenol nucleus, Q' and Q'' are the same as Q and in addition, halogen, with the proviso that Q, Q' and Q'' are all free of a tertiary alpha-carbon atom and n is a whole number of at least 50; and (ii) a styrene resin.

Polyphenylene ethers represented by the formula of component (i) above and methods for their formulation may be found in U.S. Pat. Nos. 3,306,874 and 3,305,875 of Allan S. Hay and U.S. Pat. Nos. 3,257,357 and 3,257,358 of Gelu Stamatoff.

The styrene resin (ii), as is described in the above noted Cizek patent, has at least 25 percent by weight polymer units derived from the compound having the formula:

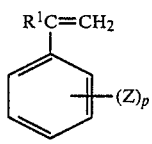

where $R^1$ is a hydrogen, (lower)alkyl or halogen; Z is a member selected from the class consisting of vinyl, halogen, and (lower)alkyl; and p is a whole number equal to from 0 to the number of replaceable hydrogen atoms on the benzene nucleus. Typical styrene resins include, by way of example, homopolymers such as polystyrene and polychlorostyrene, the modified polystyrenes such as rubber modified polystyrenes (high impact styrenes), and the styrene containing copolymers such as the styrene-acrylonitrile copolymers (SAN), styrene-butadiene copolymers, styrene-acrylonitrile-alpha-alkyl styrene copolymers, styrene-acrylonitrile-butadiene copolymers (ABS), poly-alpha-methyl styrene, copolymers of ethylvinyl benzene and divinyl benzene, and the like. (Lower)alkyl groups contain up to 6 carbon atoms.

A preferred ratio of polyphenylene ether to styrene resin comprises 20 to 80% by eight of the latter. The polyphenylene ether is preferably poly(2,6-dimethyl-1,4-phenylene)ether. The styrene resin is preferably a rubber modified high impact polystyrene as is described in the Cized patent.

The manner of adding the flame retardant mixture to the normally flammable resinous composition is not critical. Preferably, each component is added as a part of a premix, the latter being passed through an extruder with extrusion temperature being maintained between about 450° and 640° F., dependent upon the composition. The strands emerging from the extruder may be cooled, chopped into pellets, re-extruded, chopped into pellets and molded to a desired shape.

The concentration of the flame retardant mixture in the resinous composition is not critical and is dependent to a large extent upon the the degree of flammability of the normally flammable resinous composition. Where the last-mentioned composition comprises a polyphenylene ether and a styrene resin, the degree of flammability is dependent to a large extent upon the concentration of the styrene resin and the particular styrene resin used. Lower concentrations of styrene resin or less flammable styrene resins may include a lower concentration of the flame retardant. In general, a small concentration of the flame retardant is desirable, 0.5 to 15 parts per 100 parts of polymer (phr.) generally being acceptable and between 1 and 10 phr being preferred where the styrene content permits.

This invention is further illustrated by the following non-limiting examples.

EXAMPLE 1

This example illustrates the preparation of mixture of mesityl xylyl phosphates from a mixture of polymethylphenols.

To a 250 ml flask equipped with a stirrer, reflux condenser, thermometer, and heater was added 396 gm of a mixture of polymethylphenols. The mixture consisted of 75% 2,4,6-trimethylphenol, 23% 2,4 and 2,6-dimethylphenols and 2,3,6-trimethylphenol and anisoles. The phenolics were combined with 153 g of phosphorous oxychloride and 8 gm of magnesium chloride at 25° C. This mixture was heated to 250° C. for six hours and hydrogen chloride was continuously evolved. After purging the reaction mass with nitrogen, it was purified by vacuum distillating unreacted phenolics.

Gas chromatographic analysis indicated the still pot contained 95% of a mixture of triaryl phosphates after the phenolics were removed and the yield of mixed mesityl xylyl phosphates was 78%. The product mixture is transparent and glassy and has a pour point near 80° C.

EXAMPLE 2

Poly(2,6-dimethyl-1,4-phenylene)ether, 400 parts; 600 parts of rubber modified high impact polystyrene Foster Grant 834; 5 parts of diphenyl decyl phosphite, 15 parts of polyethylene, and 130 parts of mesityl xylyl phosphate are blended in a Waring blender and extruded in a 28 mm Werner Pfleiter extruder (rear, 540° F.,; front, 555° F.; die, 550° F.). The extruded pellets are again extruded under the same conditions and then molded into standard test bars on a 3 oz Newbury injection molding machine (nozzle, front, rear, all 450° F.; die, 170° F.). For comparison purposes, a second composition is made in exactly the same way except that half the mesityl xylyl phosphate is replaced with 65 g. of triphenyl phosphate and a third composition is made with 130 g of a commercial grade of isopropylphenyl phosphate mixture.

Test bars 1/16" thick of all compositions are tested for flammability, igniting the bars in a gas flame and measuring the time required for extinction of the flame in each bar according to the procedure of the U.L. 94 test, as modified. The molded pieces are also subjected to physical property measurements, the heat distortion temperature being measured by ASTM method D-648.

The results of the flame tests on 5 bars and the physical properties are set forth in Table 1:

TABLE 1

| Flammability and Physical Properties of Polyphenylene Ether and Polystyrene Compositions Containing Mesityl Xylyl Phosphate Mixture | | | |
|---|---|---|---|
| Example | 1 | 2 | 3 |
| Formulation (parts by weight) | | | |
| poly(2,6-dimethyl-1,4-phenylene)ether | 400 | 400 | 400 |
| high impact polystyrene | 600 | 600 | 600 |
| mesityl xylyl phosphate | 130 | 65 | — |
| triphenyl phosphate | — | 65 | — |

TABLE 1-continued

Flammability and Physical Properties of Polyphenylene Ether and Polystyrene Compositions Containing Mesityl Xylyl Phosphate Mixture

| Example | 1 | 2 | 3 |
|---|---|---|---|
| tri isopropyl phenyl phosphate | — | — | 130 |
| decyl diphenyl phosphite | 5 | 5 | 5 |
| polyethylene | 15 | 15 | 15 |
| Flame Test | | | |
| Average time to extinction (sec.) 1st ignition | 14 | 12 | 9 |
| Average time to extinction (sec.) 2nd ignition | 8 | 10 | 14 |
| Physical Properties | | | |
| Heat distortion temp., °F. at 264 psi. | 204 | 195 | 184 |
| Melt viscosity at 540° F. and 1500 sec$^{-1}$ | 1400 | 1200 | 1150 |
| Notched Izod Impact, ft.lbs./in. | 3.3 | 3.3 | 2.6 |
| Yellowness Index | 32 | 32 | 28 |

The composition of example 2 according to this invention has a significantly higher heat distortion temperature and is comparable in other properties.

EXAMPLE 3

Poly(2,6-dimethyl-1,4-phenylene)ether, 550.0 parts, 450.0 g. of rubber modified high impact polystyrene, 15 parts of polyethylene, 10 parts of diphenyl decyl phosphite, 1.5 parts of zinc sulfide, 1.5 parts of zinc oxide and 35 mesityl xylyl phosphate are extruded and molded as described in Example D. A second composition is prepared in the same way except that the half mesityl xylyl phosphate is replaced by 18 parts of triphenyl phosphate and a third composition is prepared from 35 parts of triphenyl phosphate.

The average flame-out time (U.L. 94 test, first ignition) is measured on five 1/16" thick bars, and the physical properties, including heat distortion temperature, are measured. The results are set forth in Table 2:

TABLE 2

Flammability and Physical Properties of Polyphenylene Ether and Polystyrene Compositions Containing Mesityl Xylyl Phosphate Mixture

| Example | 1 | 2 | 3 |
|---|---|---|---|
| Formulation (parts by weight) | | | |
| poly(2,6-dimethyl-1,4-phenylene)ether | 550 | 550 | 550 |
| high impact polystyrene | 450 | 450 | 450 |
| mesityl xylyl phosphate | 35 | 18 | — |
| triphenyl phosphate | — | 17 | 35 |
| polyethylene | 15 | 15 | 15 |
| diphenyl decyl phosphite | 10 | 10 | 10 |
| zinc sulfide | 1.5 | 1.5 | 1.5 |
| zinc oxide | 1.5 | 1.5 | 1.5 |
| Flame Test | | | |
| Time to extinction (sec.) average of 5, 1st ignition | 14 | 17 | 17 |
| Physical Properties | | | |
| Heat distortion temp., °F. at 264 psi. | 245 | 237 | 236 |
| Melt viscosity at 540° F. and 1500 sec$^{-1}$ | 2290 | 2400 | 2550 |
| Yellowness Index | 31 | 29 | 29 |
| Notched Izod Impact, ft.lbs./in. | 2.9 | 3.7 | 2.5 |

The composition of example 3 according to this invention has a significantly higher heat distortion temperature and is comparable in other properties.

It is obvious that modifications can be made in light of the above examples. For instance, poly(2,6-diphenyl-1,4-phenylene)ether can be substituted for the poly(2,6-dimethyl-1,4-phenylene)ether. For the rubber modified high impact polystyrene, there can be substituted homopolystyrene or a 80:20 copolymer of styrene and methyl methacrylate.

In addition, the compositions of this invention may be formulated with other additives, for conventional purposes, such as pigments, plasticizers, fillers, reinforcements and the like. Furthermore, third component resins such as polyethylene may be added in minor concentrations without departing from the spirit or scope thereof. The compositions are useful to form films, fibers, molded articles, and the like, in accordance with conventional practice.

What is claimed is:

1. A flame retardant composition comprising a mixture of aromatic phosphates represented by the following average formula

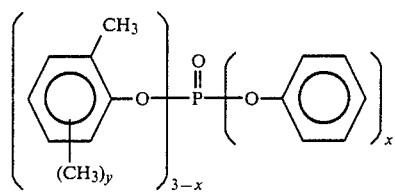

where x is zero or a whole or fractional number from slightly more than 0 to slightly less than 3 and y is a whole or fractional number from 1 to 2.

2. The composition of claim 1 wherein said mixture comprises at least 2 compounds selected from the group consisting of (a) triphenyl phosphate (TPP), (b) diphenyl mesityl phosphate (DPMP), (c) dimesityl phenyl phosphate (DMPP) and (d) trimesityl phosphate (TMP) subject to the proviso that at least one of said two compounds is selected from the group consisting of DPMP and DMPP.

3. The composition of claim 2 wherein said mixture comprises at least 3 of said compounds.

4. The composition of claim 2 wherein said mixture comprises all 4 of said compounds.

5. The composition of claim 1, wherein $\bar{y}=1$ and said mixture comprises at least 2 compounds selected from the group consisting of (a) trixylyl phosphate (TXP), (b) dixylyl mesityl phosphate (DXMP), (c) dimesityl xylyl phosphate (DMXP) and (d) trimesityl phosphate (TMP) subject to the proviso that at least one of said 2 compounds is selected from the group consisting of DXMP and DMXP.

6. The composition of claim 5 wherein said mixture comprises at least 3 of said compounds.

7. The composition of claim 5 wherein said mixture comprises all 4 of said compounds.

8. The composition of claim 5, further including tri(isopropyl phenyl)phosphate.

9. The composition of claim 2 further including tri(isopropyl phenyl)phosphate.

10. A process for decreasing the self-extinguishing time of a normally flammable resinous composition, said process comprising adding to said resinous composition an effective flame retardant amount of the flame retardant composition of claim 1.

11. The process of claim 10, wherein said resinous composition comprises a normally flammable composition comprising (i) a polyphenylene ether of the formula

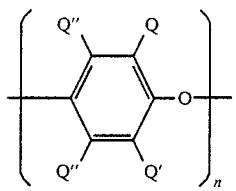

wherein the oxygen ether atom of one unit is connected to the benzene nucleus of the next adjoining unit; Q is monovalent substituent selected from hydrogen, a hydrocarbon radical, a halohydrocarbon radical having at least two carbon atoms between the halogen atom and the phenol nucleus, hydrocarbonoxy radicals and halohydrocarbonoxy radicals having at least two carbon atoms between the halogen atom and the phenol nucleus; Q' and Q'' are the same as Q and in addition, halogen with the proviso that Q, Q' and Q'' are all free of a tertiary alpha-carbon atom and n is a whole number of at least 50; and (ii) a styrene resin.

12. A process as defined in claim 11 wherein the styrene resin is present in the amount of from about 80 to about 20% by weight of the weight of components (i) and (ii) in the composition and has at least 25% by weight of units derived from a vinyl aromatic compound of the formula

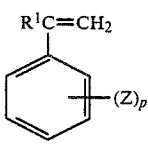

wherein $R^1$ is hydrogen, (lower)alkyl or halogen, Z is vinyl, halogen or (lower)alkyl and p is 0 or a whole number equal to the number of replaceable hydrogen atoms on the benzene nucleus.

13. A process as defined in claim 11 wherein the flame retardant composition comprises from about 0.5 to about 15 parts by weight per 100 parts by weight of component (i) and component (ii).

14. A process as defined in claim 13 wherein the flame retardant composition comprises from about 1 to about 10 parts by weight per 100 parts by weight of component (i) and component (ii).

15. A process as defined in claim 11 wherein component (i) is poly(2,6-dimethyl-1,4-phenylene)ether.

16. A process as defined in claim 12 wherein the styrene resin is a rubber-modified high impact polystyrene.

17. A resinous composition comprising (a) a resin moiety and (b) an effective flame retardant amount of the flame retardant composition of claim 1.

18. The resinous composition of claim 17, wherein said resin moiety is a normally flammable composition comprising (i) a polyphenylene ether of the formula

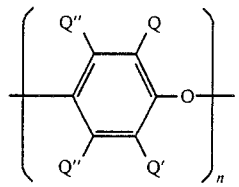

wherein the oxygen ether atom of one unit is connected to the benzene nucleus of the next adjoining unit; Q is a monovalent substituent selected from hydrogen, a hydrocarbon radical, a halohydrocarbon radical having at least two carbon atoms between the halogen atom and the phenol nucleus, hydrocarbonoxy radicals and halohydrocarbonoxy radicals having at least two carbon atoms between the halogen atom and the phenol nucleus; Q' and Q'' are the same as Q and in addition, halogen with the proviso that Q, Q' and Q'' are all free of a tertiary alpha-carbon atom and n is a whole number of at least 50; and (ii) a styrene resin.

19. A resinous composition as defined in claim 18 wherein the styrene resin is present in an amount of from about 80 to about 20% by weight of the weight of components (i) and (ii) in the composition and has at least 25% by weight of units derived from a vinyl aromatic compound of the formula

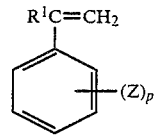

wherein $R^1$ is hydrogen, (lower)alkyl or halogen, Z is vinyl, halogen or (lower)alkyl and p is 0 or a whole number equal to the number of replaceable hydrogen atoms on the benzene nucleus.

20. A resinous composition as defined in claim 18 wherein the flame retardant composition comprises from about 0.5 to about 15 parts by weight per 100 parts by weight of component (i) and component (ii).

21. A resinous composition as defined in claim 20 wherein the flame retardant composition comprises from about 1 to about 10 parts by weight per 100 parts by weight of component (i) and component (ii).

22. A resinous composition as defined in claim 18 wherein component (i) is poly(2,6-dimethyl-1,4-phenylene)ether.

23. A resinous composition as defined in claim 19 wherein the styrene resin is a rubber-modified high impact polystyrene.

* * * * *